United States Patent [19]

Townsend

[11] Patent Number: 4,773,404

[45] Date of Patent: * Sep. 27, 1988

[54] MULTIAXIS CONTROLLED MOTION KNEE ORTHOSIS

[76] Inventor: Jeffrey H. Townsend, 2631 Parkway, Bakersfield, Calif. 93304

[*] Notice: The portion of the term of this patent subsequent to Feb. 9, 2005 has been disclaimed.

[21] Appl. No.: 89,263

[22] Filed: Aug. 25, 1987

Related U.S. Application Data

[60] Division of Ser. No. 792,770, Oct. 30, 1985, Pat. No. 4,723,539, which is a continuation-in-part of Ser. No. 639,866, Aug. 13, 1984, abandoned.

[51] Int. Cl.⁴ .............................................. A61F 5/00
[52] U.S. Cl. ................................................. 128/80 C
[58] Field of Search ............... 128/80 C, 80 F; 623/39

[56] References Cited

U.S. PATENT DOCUMENTS

| | | | | |
|---|---|---|---|---|
| 3,552,786 | 1/1971 | Schmid | ..................... | 128/80 F X |
| 4,353,361 | 10/1982 | Foster | ..................... | 128/80 C |
| 4,463,751 | 8/1984 | Bledsoe | ..................... | 128/80 C |
| 4,603,690 | 8/1986 | Skeen | ..................... | 128/80 C |

FOREIGN PATENT DOCUMENTS 412362  4/1925  Fed. Rep. of Germany .... 128/80 F Primary Examiner—Clifford D. Crowder
Attorney, Agent, or Firm—Sixbey, Friedman, Leedom & Ferguson

[57] ABSTRACT

The present invention relates to an appliance for controlling an unstable knee joint in the sagittal, coronal and transverse planes, comprising femoral and tibial cuffs joined by links which are interconnected to provide a novel mechanical joint wherein camming slots are formed in one of the links with cams disposed on the other link, the slots comprising straight segments and arcuate segments so as to provide approximately 8 millimeters of sliding movement between the femur and tibia, followed by relative rotation about the center of radius of the femoral condyle as the leg is flexed. The tibial cuff is conformed about the boney prominence or shin of the tibia to inhibit rotation of the leg beneath the knee within the brace itself.

13 Claims, 5 Drawing Sheets

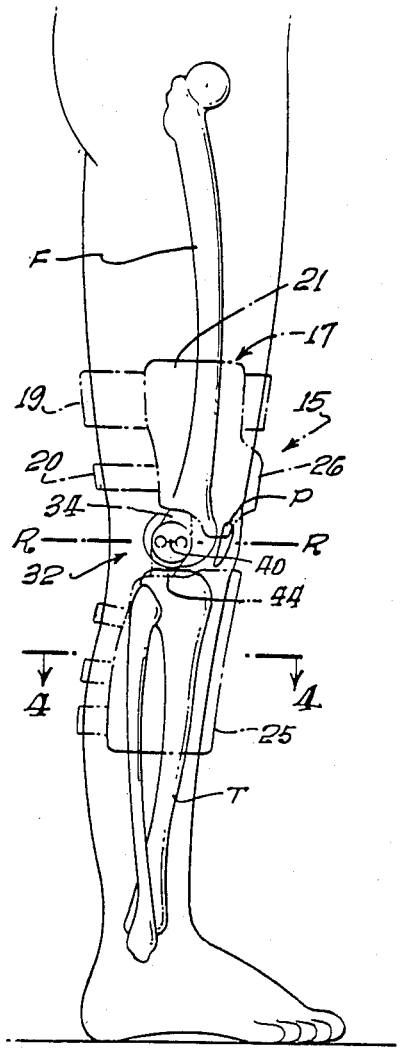
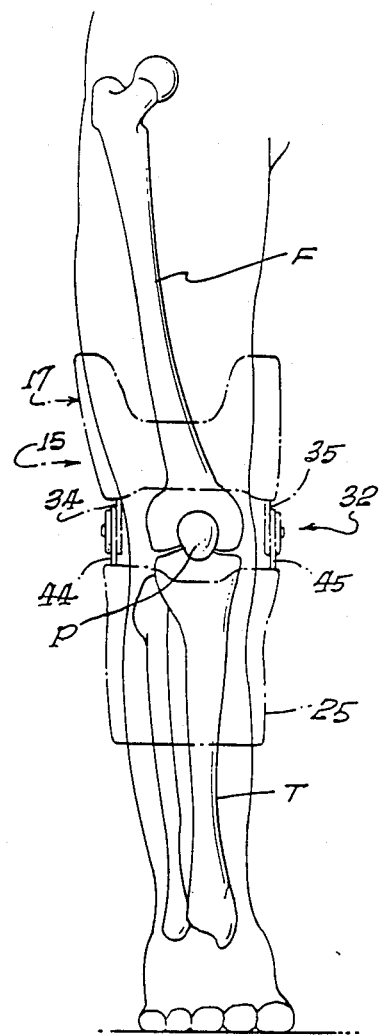

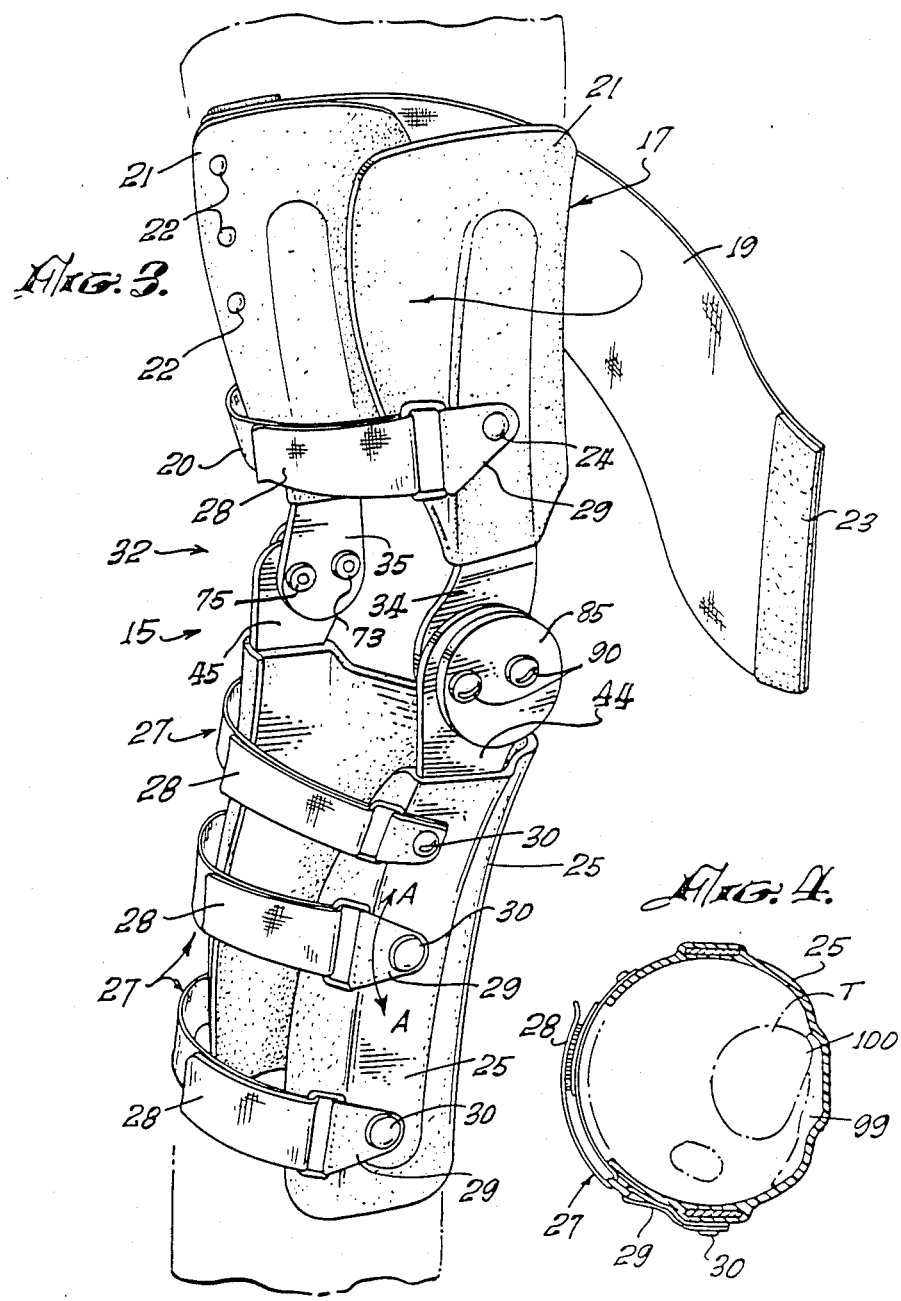

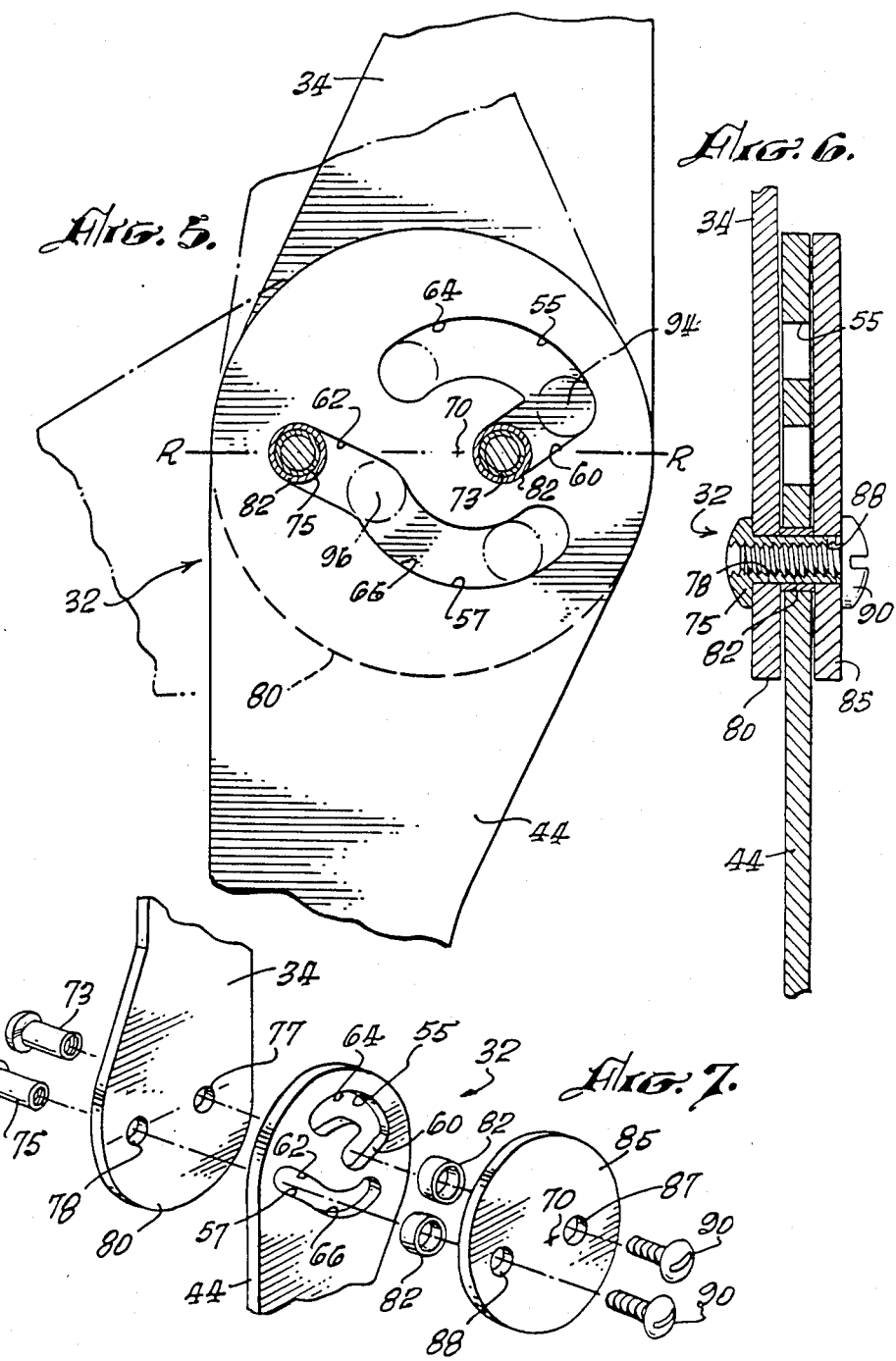

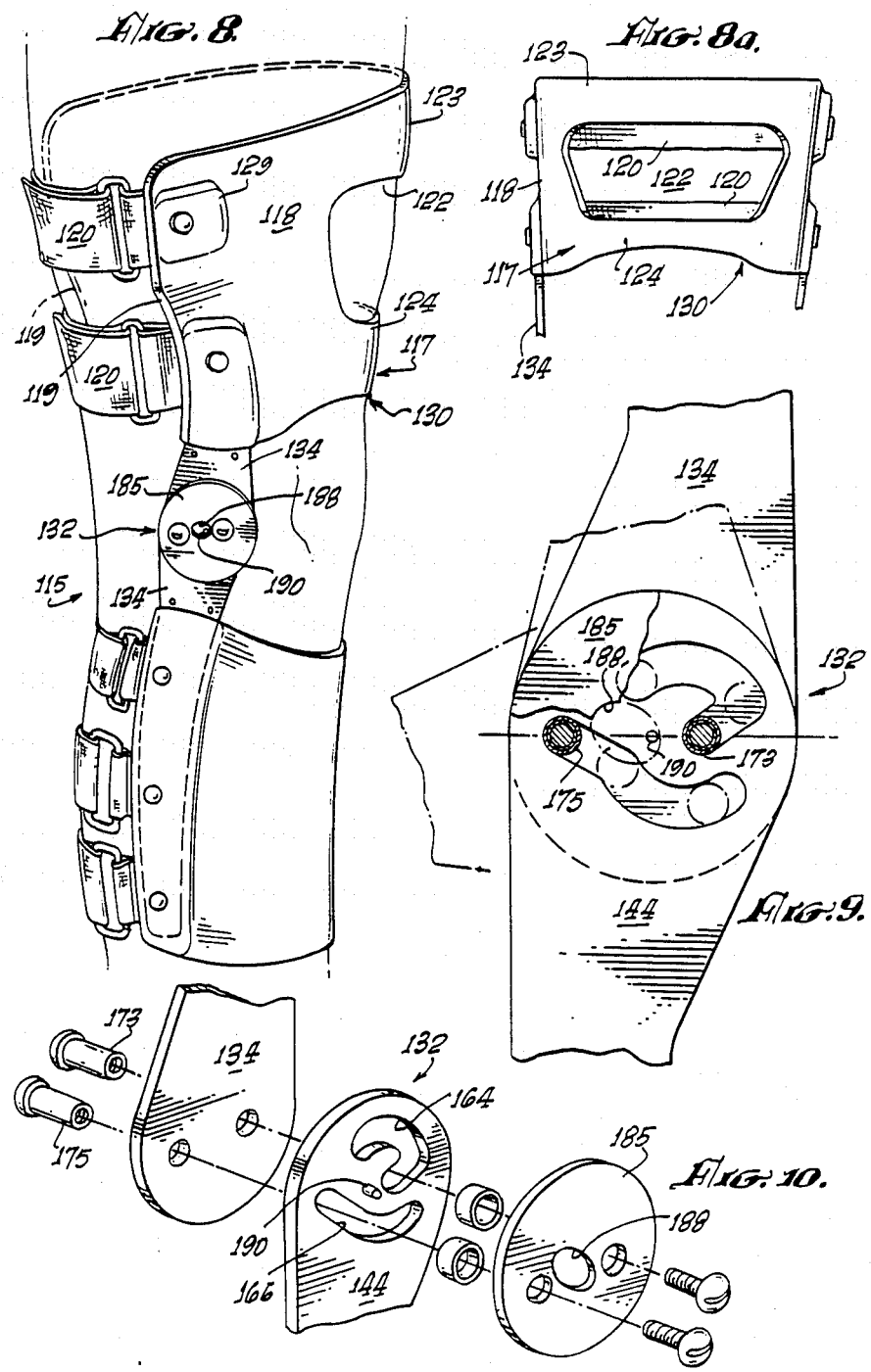

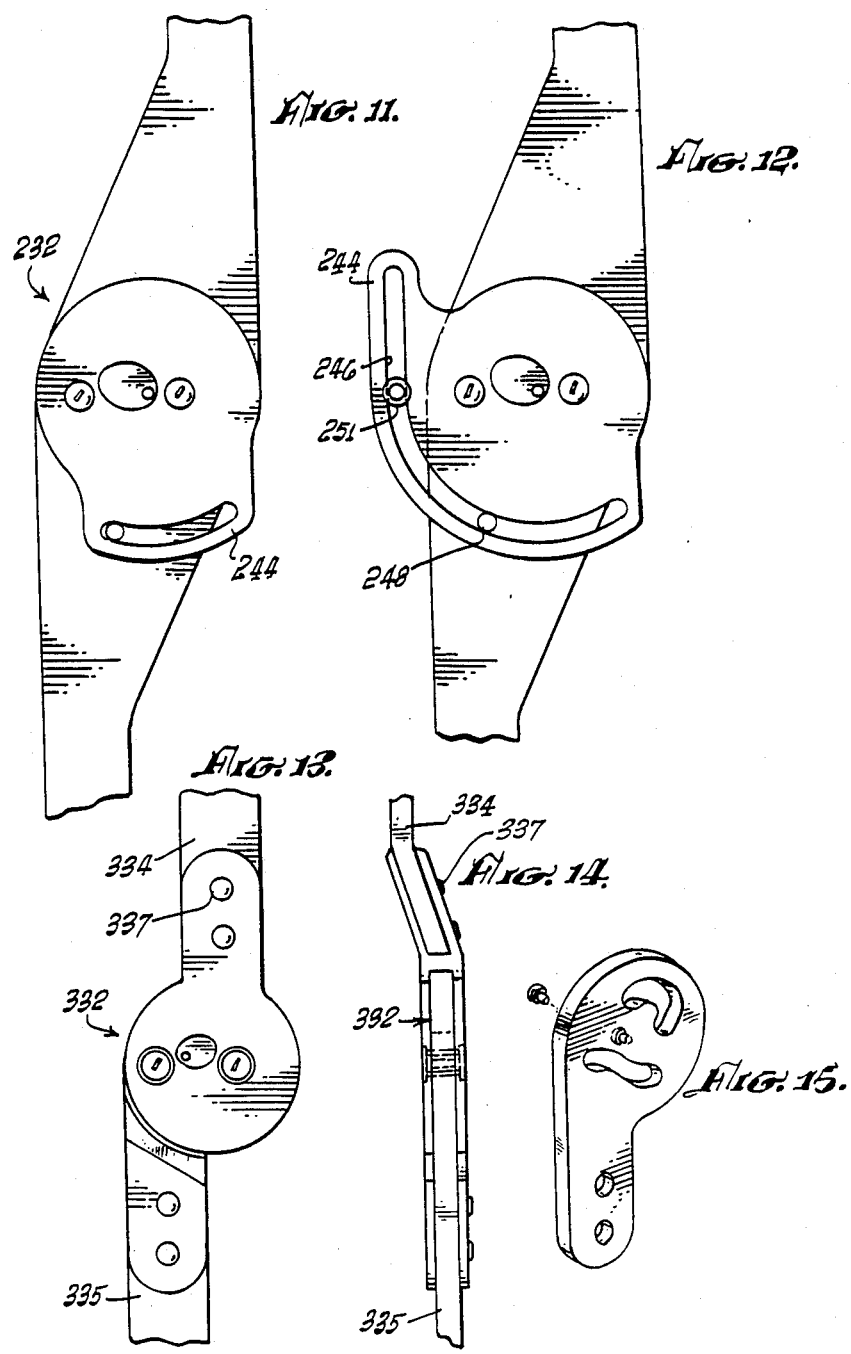

MULTIAXIS CONTROLLED MOTION KNEE ORTHOSIS

This application is a division of application Ser. No. 792,770 filed Oct. 30, 1985 now U.S. Pat. No. 4,723,539 which is a continuation-in-part of my co-pending application, Ser. No. 06/639,866 filed on Aug. 13, 1984 now abandoned.

BACKGROUND OF THE INVENTION

1. Field of the Invention

The present invention relates to orthopaedic devices for the stabilization and control of a human knee joint along several axes and has as its primary purpose the stabilization of the knee joint which has been injured. Stabilization and control is achieved in such a manner as to permit the user relative freedom in the normal use of the bones while, at the same time, permitting control over the joint so as to optimize healing.

The human knee is acknowledged as one of the weakest joints in the body. It is the articulating joint between the thigh and calf muscle groups which support the body's weight while walking or running, and it is held together primarily by two small but powerful ligaments, the anterior and posterior cruciate ligaments. Knee instability arising out of cartilage damage, ligament strain and other such causes is relatively commonplace since the knee joint is subjected to significant loads during the course of almost any kind of physical activity requiring the use of the legs. Devices for adding support and strength to the knee joint have been known at least since the very early Sears and Roebuck catalogs, which provided elasticized support members intended to circumscribe the joint to apply a squeezing pressure which results in a "feeling" of additional support even though that support may be physiologically minimal.

While the public has been sports-minded for years, it was not until the late 1960's, with a great increase in the volume of televised professional sports, and very highly paid athletes, and, in particular, contact sports such as football, basketball and soccer, that sports medicine, as a specialized field, evolved. Until that time, knee braces typically consisted of two sets of links connected by a pivot pin which were disposed on either side of the knee and sewn into an elasticized sleeve which was slipped over the knee joint like an elastic sock so that the pivot pins were disposed on either side of the knee. Such devices afforded virtually no protection to an athlete engaged in a contact sport, or in a sport where there is a large amount of stress placed on the knee joint due to running, jumping, pivoting and the like.

2. Survey of the Prior Art

Perhaps one of the first and most highly publicized breakthroughs, or at least advances in knee orthoses, occurred when the Lennox Hill brace was developed to protect the knees of Joe Namath, then one of the highest paid athletes in any sport. Several deficiencies in the Lennox Hill design have been recognized, however, and sports medicine people have spawned a plethora of other braces in attempts to improve knee stabilization. The designs include single and double pivot designs, although the double pivot design available typically includes a center link with pivot points at each end, and with the center link being axially aligned with the femur and tibia. Among such braces are included the model 4521 offered by Orthopedic Systems, Inc. of Hayward, Calif., and the polyaction knee orthosis offered by Scott Orthopedic Labs in Denver, Colo. Still another, called c.t.i. brace, is offered by Innovation Sports of Irvine, Calif.

The patent art also offers several exemplars of efforts to stabilize injured knee joints, and among them are the following patents:

Foster, U.S. Pat. No. 4,353,361; Gardner, U.S. Pat. No. 3,799,158; Deibert, U.S. Pat. No. 4,271,831; Horne, U.S. Pat. No. 3,779,654; Taylor, U.S. Pat. No. 3,902,482; Gromes, U.S. Pat. No. 1,336,695; Buring, et al., U.S. Pat. No. 4,409,689; Almedia, U.S. Pat. No. 4,139,002; and Meierhofer, U.S. Pat. No. 2,379,538.

The bulk of the prior art offerings comprise a variety of braces ranging from very simple to quite complex mechanical joints, all of which have a unity of intent, i.e., stabilization of an injured knee. Some of the braces are intended to protect and stabilize particular injuries and others are more general in their application. As will become apparent from the following detailed description of a preferred embodiment of the present invention, however, none of these prior efforts accomplished the high degree of stabilization with relative simplicity offered by the present invention.

DESCRIPTION OF THE DRAWINGS

With the foregoing as historical perspective, a preferred embodiment of the present invention will now be described in detail, which description should be read in conjunction with the accompanying drawings, wherein FIG. 1 is a lateral side elevation of the orthosis of the present invention shown as mounted to the right leg of the user;

FIG. 2 is a front elevation of the same leg showing the orthosis in a different aspect;

FIG. 3 is a perspective of the orthosis showing the overall construction, and the arrangement for mounting the same, in its operative position, on the user's leg;

FIG. 4 is a sectional view of the orthosis, mounted on the leg, taken along section 4—4 of FIG. 2, and is intended to show the relative position of the orthosis with respect to the tibia and the calf area of the leg, to illustrate one of the unique features of the invention;

FIG. 5 is a side elevation of a typical joint of the present invention, indicating the relative position of the components at various stages of flexion of the knee;

FIG. 6 is a side elevation, in partial section, showing the knee joint of FIG. 5;

FIG. 7 is an exploded perspective view of a typical joint of the present invention, showing the relative interfitting arrangement of components thereof.

FIG. 8 is a lateral side elevation of the orthosis of the present invention shown as in FIG. 1, mounted to the right leg of the user, and illustrating certain alternative embodiments, particularly of the femoral cuff and joint mechanism;

FIG. 8a is a front elevation of a portion of the femoral cuff of FIG. 8 illustrating the features thereof, from a slightly different perspective;

FIG. 9 is a side elevation of an alternative form of the joint mechanism of FIG. 5;

FIG. 10 is an exploded perspective view of the joint mechanism illustrated in FIG. 9;

FIGS. 11 and 12 are side elevations of the joint mechanism illustrating modifications thereof to permit limitation of extension and flexion of the knee joint;

FIG. 13 is a side elevation of a pair of links joined at their respective terminus by a joint mechanism to form an articulating strut constructed in accordance with the present invention for use with various orthopaedic appliances;

FIG. 14 is a side elevation of the joint of the strut mechanism of FIG. 13; and

FIG. 15 is an exploded perspective view of the camming link of the strut assembly shown in FIG. 13.

DETAILED DESCRIPTION OF THE PREFERRED EMBODIMENT

With reference now to the drawings, and more particularly to FIGS. 1 and 2, a multiaxis controlled motion knee orthosis, or brace, 15 is depicted in its proper mounted position on the right leg of a wearer. So that the fit of the orthosis may be clearly understood, the drawing also depicts the relative positions of the femur F and the tibia T as well as the patella P, forming a ... typical knee joint of an adult male, indicating the alignment of each with respect to the brace 15, with the wearer standing erect and the right leg in the longitudinally extended position. The brace 15, as may be seen best in FIG. 3, includes means for securing the brace to the leg of the wearer, comprising a pair of leg grasping devices in the form of an upper thigh, or femoral, cuff 17 having a major closure means 19 and a minor closure means 20, both of which are constructed so as to secure and snugly fit the thigh within the cuff 17.

The major closure means encircles the entire upper thigh and is, preferrably, of an elastic material, e.g. Latex, so as to provide some give as the muscles are flexed, and may be of a Latex material, or such other suitable elastic fabric, as desired. The femoral cuff includes a pair of opposed spaced wings 21, adapted to engage the lateral and medial sides of the thigh. The major closure is attached to the medial wing, such as by rivets 22, and a Velcro closure is provided as at 23. The minor closure 20, attaches to the lateral wing at pivot pin 24 and, as illustrated, employs a "D" ring through which the closure is fed and doubled back on itself to provide the desired firmness of fit. Once again, a Velcro closure, or some other closure, is employed.

A calf, or tibial, cuff 25 is disposed beneath the knee joint and partially encircles the calf area, as best seen in FIGS. 1 and 2. In order to ensure snug fit of the tibial cuff 25, there are provided transverse closure members 27, of which three are shown in longitudinally spaced relation. In order to assure a more precise fit, the femoral and tibial cuffs are formed to specially fit the exact leg upon which the brace is to be worn. This is accomplished by forming a cast about the leg of the intended wearer. The cast is then cut and thereupon serves as a mold to form a model of the leg. Each cuff is then precisely fabricated of a laminate material right on the cast in the proper position. In order to provide optimum strength, both graphite and Kelvar filaments are used in a liquid resin, which is then formed about a casting to create the cuffs. Thereafter, the cuffs are lined with some suitably resilient, shock absorbent material such as, for example, sorbathane, and are ready to wear.

The femoral cuff 17, as previously described, is formed with a pair of wings positioned relative to one another by a bridge section 26 spanning the lower part of the thigh above the knee. This construction allows some freedom to allow the larger, upper thigh muscles to expand and contract with loss of control. The area engaged by the tibial cuff includes the greater portion of the calf muscle at the rear of the leg. For that reason, the tibial cuff is more "C" shaped, encircling the majority of the anterior portion of the lower leg, as seen in FIG. 4. The cuff is open at the rear of the leg to permit the cuff to be slipped on, and, further, to permit flexing of the calf muscle when the cuff is in place.

The closure members 27 are of a similar construction to the minor closure member 20 secured to the femoral cuff. Thus, each member includes an elastic strap 28 riveted, or otherwise secured, at some point on the medial side of the cuff. A "D" ring is affixed in the lateral plane of the strap by means of a hanger 29 which is shown as attached to the lateral side of the cuff by a fastener 30. The fastener, which may be of any suitable construction, permits limited, essentially longitudinal positioned adjustment by rotation of the hanger 29 along a path A—A so as to permit snug fit over the severe contours of the calf as it flexes during movement. As before, the strap may pass through the "D" ring and close by means of Velcro, or some other suitable closure means.

While the formation and construction of the femoral and tibial cuffs is an important aspect of the invention as a whole, a major feature of the invention rests in the construction of the unique mechanical joint 32, which joins the cuffs to define the brace 15 into an orthosis capable of stabilizing the wearer's knee joint in each of the transverse, coronal and sagittal planes. The detailed construction of the joint 32 of the present invention will now be described with respect to such a joint position at the lateral side of the right knee. It will be appreciated that the medial joint is the mirror image of the lateral joint, and that both will operate in unison as the leg is flexed.

With reference first, primarily, to FIG. 3, the femoral cuff 17 is provided with depending, spaced apart, parallel supporting links 34 and 35 respectively. As seen in FIG. 3, link 34 is the lateral link and link 35 is the medial link. The links 34 and 35 are readily laminated into the tibial cuff, in a known manner, although it will be appreciated that they may be sewn in, or otherwise fastened, without departure from the invention. The free end of each link 34 and 35, terminates in a bulged, or widened, end. As previously stated, the links are essentially parallel and are disposed on the medial and lateral sides of the thigh, respectively, and depending therefrom to and through a transverse plane R—R as shown in FIG. 1. The plane R—R is transverse to the longitudinal plane of the tibia F and passes through a center point 40, which represents the center of radius of rotation of the femoral condyle relative to the tibia.

In a like manner, the tibial cuff 25 is provided with upwardly extending, spaced parallel links 44 and 45, respectively, link 44 being on the lateral side, and link 45 being on the medial side of the cuff, as shown. As in the case of the femoral links 34 and 35, the tibial links 44 and 45 extend upwardly, passing through the transverse plane R—R, and each terminates in a widened, or bulged, portion. As in the case of the femoral links, the tibial links may be molded into, sewn, or otherwise attached, to the tibial cuff in some convenient well-known manner. Once again, referring to FIG. 3, it will be seen that the lateral femoral and tibial links 34 and 44 are essentially aligned in adjacent planes such that the terminus of each of the links overlaps and is disposed immediately adjacent to one another in a transverse plane, as is the case with the medial links. In each case, the femoral links are disposed slightly inwardly of the tibial links, once again, as best seen in FIG. 6.

Overlapping bulged termini portions of the respectively lateral and medial links intersect and lie within the plane R—R to provide the nucleus of the highly unique joint mechanism indicated generally at 32 and illustrated in detail in FIGS. 5, 6 and 7, respectively. In order to provide optimum stability for an injured knee, and particularly a knee in which the injury involves either the anterior or posterior cruciate ligament, it is necessary to emulate, insofar as reasonably possible, natural, relative movement of the femur and tibia. Most prior art devices appear to have taken for granted that such movement consists of a relative rotation about a single center of rotation, typically in the center of the knee, which is the philosophy resulting in the familiar single pivot brace. Since that is not the natural relative movement of the knee joint, such single pivot braces inherently cause undue stress during flexion of the knee joint, rather than stabilizing, which is the ultimate goal of the present brace. In fact, it has been found that commencing from the leg extended position, the initial movement of the tibia relative to the femur through the first 25° of flexion is an approximately 8 millimeter front to rear slide, followed by rotation as the knee continues to flex through a 125° angle, or for whatever angle may be traversed, as limited by the injury or natural limitations. It has been determined that if the knee is permitted to move in a natural fashion, stress on the cruciate ligaments and the quadriceps muscles, which play a major role in the function of the knee, is so minimal that an injury to the knee is actually permitted to heal more effectively when the user wears the brace of the present invention.

With the foregoing biomechanics in mind, the joint mechanism of the present invention is constructed to permit the knee joint to be constrained to move with the natural glide and rotation of a normal knee, to, thereby, protect the injury and minimize stress by the provision of spaced camming devices, which as illustrated, take the form of longitudinally spaced camming slots 55 and 57, respectively. For the purposes of identification, the camming slot 55 will be referred to as the femoral camming slot and camming slot 57 may be referred to as the tibial camming slot. Each slot is formed in a straight line segment 60 and 62, respectively, which adjoins arcuate segments 64 and 66, respectively. It will be noted that the straight line segments 60 and 62 terminate at the end remote from the juncture with the arcuate segments 64 and 66 on the plane R—R. It will also be noted that the arcuate segments are generated about the same radial center which is aligned with the center point 40.

The camming slots are adapted to receive and operate in conjunction with the camming follower means, which, as illustrated, comprise screws 73 and 75. As illustrated in FIG. 7, a two-part post and screw assembly manufactured by Chicago Screw is shown, although other forms of camming devices could be employed. The camming screws 73 and 75 pass through holes 77 and 78 formed in the terminus 80 of the femoral link (free end). The holes 77 and 78 lie in plane R—R. Bushings 82 are provided, having an inside diameter sufficient to fit over the circumferential surfaces of the posts 73 and 75 in bearing relation with respect thereto, and an outside diameter sufficient to snugly fit in bearing relation within the slots 55 and 57, respectively. A cap, or cover plate, 85 having holes 87 and 88, respectively, permit the receipt of posts 73 and 75, which are then secured by screws 90 to form the joint. The cover plate not only holds the screws, but further serves as a reaction member, sandwiching the bulged terminus of the tibial link between the plate 85 and the bulged terminus 80 of the femoral link, as best seen in FIG. 6, such that relative movement of the femoral link relative to the tibial link is strictly controlled by movement of the posts 73 and 75 in the slots 55 and 57, respectively. In FIGS. 5, 6 and 7, there is shown, by way of example, a lateral joint for the right leg. The medial joint is the mirror image of the lateral joint, so that the relative movement of the lateral and medial links are coordinated and the same.

In order to achieve optimum relative natural movement of the knee joint, which, of course, is a principal feature of the present invention, the interaction of the femoral and tibial surfaces must be taken into account. To this end, while both straight segments 60 and 62 begin with pins 73 and 75, resting in plane R—R, when the leg is extended and essentially straight (see FIG. 5), as flexion begins, there is an approximate 8 millimeter lateral movement between the tibial and femoral surfaces, which is permited as the pins slide along the straight segments 60 and 62. In a very tall person, the slide may be slightly longer, and in a small child, it may be shorter, and the precise length of the slot may be adjusted to meet specific conditions. A range of 6 to 9 millimeters meets most needs. The slide of the femur and tibia, however, does not take place in plane R—R, but, rather, a slight relative tilt is experienced as the leg is flexed through the first 25° of flexion. To accommodate this movement, the straight line segment 60 forms a 50° angle with the plane R—R, whereas, the straight segment 62 forms an angle of 56° 30'. Thus, as the leg is flexed through the first 25° of flexion, camming posts 73 and 75 respectively, move in a straight line along the straight segments 60 and 62, each at the previously disclosed angle. There is a small tolerance permitted to meet specific needs, but most needs are met within ±2° of the angles herein specified. At 25°, they intersect the arcuate sections 64 and 66, respectively, at intersections 94 and 96. Beyond 25° of flexion, the natural movement of the knee through further flexion is a relative rotation of the tibia relative to the center point 70 on the femoral condyle. In order that this movement may be emulated with the greatest possible accuracy, arcuate sections 64 and 66 have been formed around center point 70 and it has been found that a radius of 0.43 inches, or 11 millimeters, provides the desired resultant rotational movement in a typical knee. Approximately 96° 30' is required to provide full knee flexion. It will be appreciated, however, that if a lesser knee flexion is required because of the particular instability found in the user's knee, the arc may traverse a greater or lesser angle without departure from the invention. Indeed, stops may be used to limit flexion simply by inserting a blocking device of known construction and, therefore, not shown, at the appropriate point within the slot 55 and 57 to thereby limit the amount of flexion that the user can experience using the brace.

While in a normal knee there is a slight outward rotation of the tibia relative to the femur upon flexion, such rotation may be pronounced in the case of certain knee injuries resulting in instability. The present invention, in still another of its inventive aspects, limits and constrains such rotation upon flexion of the knee, thereby enhancing the stability thereof. This is accomplished, as best seen in FIG. 4, by forming, or molding, the tibial cuff over the anterior boney prominence 100 of the tibia, sometimes referred to as the shin. As seen in FIG. 4, the cuff has been molded, or formed, about that prominence, such that any tendency of the tibia to rotate about its longitudinal axis upon flexion is resisted by the cuff. The structure of the cuffs and links is of such integrity that not only is rotation controlled within the cuff, but when the leg is flexed, the wings 21 of the femoral cuff, work with the tibial cuff by acting against the wearer's thigh through the links to resist any rotation of the brace, thereby totally inhibiting undesirable rotation. In order to avoid irritation by rubbing of the tibia against this tightly molded section of the cuff, a spongey material, such as sorbathane, may be provided in this area about the interior of the cuff, at or about the location 99, or about the entire area which contacts the skin of the wearer if it is so desired. Strong closure members 27, 28 and 29, of course, permit the tibial cuff to be held in position firmly against the shin, while at the same time, minimizing the discomfort which might otherwise be experienced by the wearer.

With particular reference now to FIGS. 8 through 10, several novel alternative structures are illustrated in detail. In stabilizing many injuries, it is essential to minimize torsional rotation of the femur and upper thigh relative to the lower legs. To this end, and with reference to FIG. 8, an orthosis 115 is illustrated in which a femoral cuff 117 is provided having a novel construction particularly adapted to accomplish the minimization of tortional or twisting movement of the femur and upper thigh relative to the lower leg of the wearer.

The beneficial features of this modified femoral cuff 117 are accomplished by the provision of a continuous band 118 which is molded about the thigh, embracing the same for approximately 120° of its circumference. The termini of 119 of the band 118 respectively define a rearwardly facing opening through which the users leg may pass to be positioned within the cuff 117. A pair of spaced minor closure means 120 are provided of a construction very similar to that described in connection with FIG. 3. The overall design, however, may be streamlined by molding the closure hanger 129 into the cuff.

As best seen in FIG. 8a, the femoral cuff is further formed with a laterally extending opening 122 defined by upper and lower ribs or bridges 123 and 124 respectively formed integrally with opposed, integrally formed side members or wings similar to those depicted in FIG. 3.

The femoral cuff of FIG. 8, like that of FIG. 3, is an integral unit formed of fiberglass or other moldable material and is constructed to encircle a major portion of the thigh in order to firmly but comfortably hold the upper leg against torsional rotation with respect to the lower leg. The void 122 which has the appearance of an elongated ellipsoid, preferably formed by the removal of material from the cast cuff, and results in a significant lightening of the cuff while maintaining its strength. Foam rubber or other material of like property is preferably attached, as at 27 in order to minimize abrasion between the brace and the wearer's skin and to further add to the comfort of the wearer.

Still another feature of the modified femoral cuff as shown in FIGS. 8 and 8a is seen where the lower bridge 124 is formed, along its lower edge, with a longitudinal narrowing as at 130 which further adds to the comfort of the wearer by minimizing pressure on the quadriceps muscles and the upper part of the patella when the lower leg is in extension.

Referring now to FIGS. 9 and 10 respectively, yet another embodiment of one aspect of the invention is illustrated in some detail. Depicted in those figures is an alternative embodiment of the mechanical joint itself. As in FIG. 7, a mechanical joint 132 is illustrated in FIG. 10 as comprising a link 134 depending from the femoral cuff for limited rotational engagement with an upwardly extending tibial link 144. As described with respect to FIG. 7 arcuate segments 164 and 166 are formed in the bulging terminal end of the link 144 and posts 173 and 175 are mounted in, and pass through the link 144 and through the arcuate segments 164 and 166 respectively where they are held in place by a cover plate 185.

The arcuate segments 164 and 166 will be seen to govern the relative movement of the links 134 and 144 respectively. It will also be evident that there is significant surface area contact between the links themselves as well as between the link 144 and the cover plate 185. As a consequence of the relatively large surface area of contact, it has been found that there is a tendency, in some instances, for the joint to bind, or otherwise stated, to respond to the friction between the relative elements by a reduction in the smoothness and evenness with which the joint is articulated. In order to alleviate this possible occurrence without effecting the operation of the joint itself, the cap or cover plate 185, in accordance with the invention, is formed with an opening 188 disposed about the center point 170 of the joint. At the center point, a post 190 is attached to and extends laterally outwardly from the link 144 where it projects into the opening 188 when the joint is fully assembled. The opening 188 effects a small but significant reduction in frictional drag thereby virtually eliminating the lack of smoothness in articulation of the joint which might otherwise result from a binding effect. The post 190 projecting into the opening 188 acts as a further guide to retain the relative positions of the link 144 and the cover plate 185 in order to assure that the articulation of the joint is fully controlled by the posts 173 and 175 moving within the arcuate segments 164 and 166 respectively.

In certain cases, an orthopaedic injury or deformity calls for a restriction in the flexion and extension of the articulating knee joint to assure that the user cannot injure him or herself by either extending or flexing beyond a desirable limit. Another aspect of the invention is to provide, in such cases, means for controlling flexion and/or extension of the knee joint of the wearer. This may be accomplished by another novel modification of a mechanical joint 232 as best illustrated in FIGS. 11 and 12 respectively. As seen in those figures, the terminal end of either the tibial or femoral link may be formed with an enlarged and extended end portion 244, which may encompass several degrees of circumference. The invention contemplated the formation of a slot 246 in the extension 244, and the provision of a laterally extending post 248 on the contiguous link. The post 248 laterally extends into the slot opening 246, the slot having a curvature to permit smooth articulation of the mechanical joint throughout the full length of the slot. The desirable result is clearly that the amount of flexion and/or extension which the articulating joint may experience may be limited. In FIG. 11, for example, a traverse of the entire slot distance would limit movement to 45° whereas in FIG. 12 the limitation would be 90°. It will be understood that any limitation on movement may be achieved by controlling the length of the slot. Additionally, limitation may be adjusted as desired to a precise degree by using stop members 251 which may comprise a screw or rivet or any other device mounted within the slot to limit travel of the post 248.

In the case of certain specific injuries or deformities, or in still other instances, such as in the preparation and the manufacture of prostheses, it is desirable to be able to provide a mechanical joint at the knee position which can be molded into a plaster or fiberglass cast, or become an integral part of a prosthetic device. In light of the fact that the mechanical joints 32, 132 and 232 of the present invention provide an extremely close assimilation of the movement of a normal knee, the provision of joints which may become parts of other appliances and/or a cast or casts or various orthotic devices is a further desirable feature of the invention. This is accomplished as can be seen in FIGS. 13 through 15, by the provision of elongated parallel links 334 and 335 to which a joint 332 may be riveted or otherwise attached as at 337. The links 334 and 335 may be integrated into any prosthetic device or casts in order to provide the wearer with a natural knee joint movement. While throughout this application the various aspects of the invention have been illustrated and discussed with respect to an exemplary joint, it will be understood that joints are used in pairs on the medial and lateral side of each knee joint.

Having now described a preferred embodiment of the invention, what is claimed is:

1. In an appliance for stabilizing a knee joint in sagittal, coronal and transverse planes, having leg grasping means for clasping the appliance to the wearer's leg above and below the knee,
    means defining a mechanical joint at the medial and lateral sides of the knee, each comprising
    a pair of depending opposed femoral links, each said link terminating in an end portion,
    a pair of opposed upwardly extending tibial links terminating in an end portion; said end portion of said tibial links being disposed in overlapping relation to said end portion of said femoral links,
    cam means interconnecting each said end portion of said femoral links to a respective said end portion of said tibial links, said cam means being disposed at lateral and medial sides of the knee,
    each said cam means comprising a cam pin follower and a camming slot means, each said cam pin follower means being fixedly positioned relative to a link of one of said pairs of links and relatively displaceable relative to a link of the other of said pairs of links within a respective camming slot means, said cam pin follower and camming slot means forming a means for constraining the tibia to slide rearwardly relative to the femur for a predetermined distance during an initial range of flexion of the knee from a straight leg position and, beyond said initial range of flexion to, thereafter, rotate relative thereto in a predetermined arcuate path, irrespective of the loading applied thereto by the leg of the wearer.

2. An appliance according to claim 1, wherein said initial range of flexion is about 25°.

3. An appliance according to claim 2, wherein said arcuate path is a circular segment.

4. An appliance according to claim 1, wherein said arcuate path is a circular segment.

5. An appliance according to claim 1, wherein said camming means comprises a pair of cam pin followers and a pair of camming slot means, said cam pin followers resting in a plane that is transverse to the longitudinal plane of the tibia of the wearer and passes through a center point representing the center of the radius of rotation of the femoral condyle of the wearer relative to the tibia, and said pair of camming slots comprising upper and lower camming slots which extend from said plane in directions above and below said plane, respectively.

6. An appliance according to claim 5, wherein said initial range of flexion is about 25°.

7. An appliance according to claim 6, wherein said arcuate path is a circular segment.

8. An appliance according to claim 5, wherein said arcuate path is a circular segment.

9. An appliance according to claim 1, wherein said cam means is exclusively composed of components that are rigidly secured to at least one or the other of said femoral and tibial links.

10. In an appliance for stabilizing a knee joint in sagittal, coronal and transverse planes, having leg grasping means for clasping the appliance to the wearer's leg above and below the knee,
    means defining a mechanical joint at the medial and lateral sides of the knee, each comprising
    a pair of depending opposed femoral links, each said link terminating in an end portion,
    a pair of opposed upwardly extending tibial links terminating in an end portion; and
    connecting means interconnecting each said end portion of said femoral links to a respective said end portion of said tibial links, said connecting means being disposed at each of lateral and medial sides of the knee and being comprised of elements which coact to form a movement control means for constraining the tibia to slide rearwardly relative to the femur for a predetermined distance throughout an initial range of flexion of the knee from a straight leg position and, beyond said initial range of flexion, to rotate relative thereto along a predetermined arcuate path, irrespective of the loading applied thereto by weighting of the leg of the wearer.

11. An appliance according to claim 10, wherein said initial range of flexion is about 25°.

12. An appliance according to claim 11, wherein said arcuate path is a circular segment.

13. An appliance according to claim 10, wherein said arcuate path is a circular segment.

* * * * *